United States Patent
Hunyor et al.

(10) Patent No.: US 6,918,870 B1
(45) Date of Patent: Jul. 19, 2005

(54) ASSIST DEVICE FOR THE FAILING HEART

(75) Inventors: Stephen Nicholas Hunyor, Gordon (AU); Serguei Michael Plekhanov, Hornsby (AU); Yifei Huang, Artarmon (AU)

(73) Assignee: Heart Assist Technologies PTY LTD, St. Leonards (AU)

( * ) Notice: Subject to any disclaimer, the term of this patent is extended or adjusted under 35 U.S.C. 154(b) by 404 days.

(21) Appl. No.: 10/009,631

(22) PCT Filed: Jun. 15, 2000

(86) PCT No.: PCT/AU00/00665

§ 371 (c)(1),
(2), (4) Date: Dec. 12, 2001

(87) PCT Pub. No.: WO00/78375

PCT Pub. Date: Dec. 28, 2000

(30) Foreign Application Priority Data

Jun. 17, 1999 (AU) ............................................. PQ1006

(51) Int. Cl.[7] ............................................. A61N 1/362
(52) U.S. Cl. ..................................................... 600/16
(58) Field of Search ............................ 600/16, 17, 37, 600/374, 479, 481, 508, 587; 623/3.1, 3.11, 3.17, 3.21, 3.28, 3.29; 128/897, 898, 899

(56) References Cited

U.S. PATENT DOCUMENTS

| | | | |
|---|---|---|---|
| 4,536,893 A | | 8/1985 | Parravicini ...................... 623/3 |
| 4,925,443 A | * | 5/1990 | Heilman et al. ............... 600/16 |
| 5,098,369 A | | 3/1992 | Heilman et al. ............... 600/16 |
| 5,119,804 A | | 6/1992 | Anstadt ........................ 128/64 |
| 5,169,381 A | | 12/1992 | Snyders ........................ 600/16 |
| 5,683,364 A | * | 11/1997 | Zadini et al. ............. 604/98.01 |
| 5,713,954 A | | 2/1998 | Rosenberg et al. ............. 623/3 |
| 5,733,538 A | | 3/1998 | Riffle ....................... 424/78.08 |
| 5,749,839 A | | 5/1998 | Kovacs ........................ 601/153 |
| 5,848,962 A | | 12/1998 | Feindt et al. ................. 600/16 |
| 5,910,124 A | | 6/1999 | Rubin ......................... 601/153 |
| 5,971,911 A | | 10/1999 | Wilk ........................... 600/18 |
| 6,183,411 B1 | | 2/2001 | Mortier et al. ................ 600/16 |
| 6,206,820 B1 | | 3/2001 | Kazi et al. ................... 600/16 |
| 6,432,039 B1 | * | 8/2002 | Wardle ........................ 600/37 |
| 6,540,699 B1 | * | 4/2003 | Smith ......................... 600/587 |

FOREIGN PATENT DOCUMENTS

| | | |
|---|---|---|
| HU | P9901479 | 8/1999 |
| WO | WO98/55165 | 12/1998 |

OTHER PUBLICATIONS

Artrip, John H., MD, et al, "Hemodynamic Effects of Direct Biventricular Compression Studied in Isovolumic and Ejecting Isolated Canine Hearts," Apr. 27, 1999, American Heart Association, pp. 2177–2184.

Hotei, H. et al, "Development of a Direct Mechanical Left Ventricular Assist Device for Left Ventricular Failure," Artificial Organs, vol. 21(9), Sep. 1997, pp. 1026–1034.

* cited by examiner

*Primary Examiner*—George Manuel
(74) *Attorney, Agent, or Firm*—Steptoe & Johnson LLP; D. Douglas Price

(57) ABSTRACT

A heart actuator device for use in heart assist apparatus, which device includes a paddle-like main body. The main body has a heart compressing wall, which in use is adapted to be affixed to at least a region of heart, and a distal wall, which in use is adapted to be distal that region of the heart. The heart compressing wall is movable in a direction relatively away from the distal wall, so as, in use to compress at least that region of the heart thereby assisting movement of the heart wall.

31 Claims, 5 Drawing Sheets

ASSIST DEVICE FOR THE FAILING HEART

FIELD OF THE INVENTION

The present invention relates to a device and method for assisting a failing heart.

BACKGROUND ART

Cardiac compression has been used to boost a failing heart for many years and in its most simple life-saving form involves the compression of the chest wall of a patient. In an emergency situation, a surgeon may take this one step further by manually compressing a heart that has failed, until recovery or an alternative treatment is instituted.

Of course, not all patients present in an acute state and typically a heart will be damaged over a period of time. This can also result in heart failure, a situation which occurs when the heart fails to maintain sufficient circulation of blood to provide adequate tissue oxygenation. Heart failure is widespread in the community affecting for example, 5 million Americans at any one time. Despite recent advances in cardiology, it remains on the increase.

Mechanical heart assist devices that can be used to boost an ailing heart have the potential to provide a quality of treatment that seriously challenges current treatment options, including heart transplantation. Whilst heart transplantation is effective in patients with severe heart failure, the shortage of donor hearts, the expense of the operation and post-operative care, and the risk of rejection are major drawbacks to this option ever fulfilling community expectations.

Several mechanical devices have been developed, one of which is the subject of U.S. Pat. No. 5,119,804 to Anstadt. This device comprises a cardiac massage cup adapted to fit loosely over a lower portion of a heart. A diaphragm is positioned internal the cup and positive and negative pressure applied to the space between the diaphragm and the cup to alternately inflate and deflate the diaphragm. When the diaphragm is inflated, the heart is squeezed to assist systolic action (ejection of blood from the ventricles of the heart). The diaphragm is deflated to correspond with diastole (relaxing of the heart muscle and filling of the heart pumping chambers with blood). The cup itself is held in place around the heart by a suction force which prevents the heart from dislodging when compressive pressure is applied to the heart.

The requirement that the diaphragm be set inside a cup results in a bulky device which may also cause damage to the heart muscle, coronary circulation and the surrounding tissue.

Variations of the Anstadt cup have been developed including the device subject of U.S. Pat. No. 5,713,954 which describes a cuff to enclose the lower regions of the heart. The cuff comprises a series of closed tubes which may be hydraulically or pneumatically inflated in synchrony with the natural contractions of the heart to reinforce the contractile force required to eject sufficient blood for the needs of the body. Literature reports have shown the enhancement of heart pumping by other currently described cardiac compression devices to be limited to between 10 and 15%.

A drawback of several assist devices is that the right and left ventricular pumping action of the heart is simulated using a single diaphragm. It is well recognised, however, that differences exist between right and left ventricular output and that right and left ventricular pressures are different. Essentially, because the left ventricle is ejecting blood to the entire body it requires a greater force of contraction. Devices with only one diaphragm will not assist to provide optimum output of either the right or the left ventricle. A device designed to address this problem is described in U.S. Pat. No. 5,749,839 to Kovacs wherein the assist device is provided with two independently operated diaphragms within a cup to allow for independent control of the left and the right ventricles. This device does not seem, however, to take into account the difference in curvature between the surface of the left-and right ventricles and uses a diaphragm of the same shape for both ventricles. This would seem to potentially result in a misfit of the device over the heart if used in this manner.

With the cardiac assist devices described above, there must be a means for securing the device to the external surface of a heart. Securement may be achieved by applying suction through a vacuum line, such as is the case in the Anstadt device, wrapping the device in a passive mesh which may be fitted around the heart, by suturing or by some form of adhesive. Whichever means is employed, there is a risk of damage to the heart and in particular to the coronary circulation which is made up of a network of blood vessels that traverse the outer surface of the heart.

In International Application No. PCT/AU98/00433 (WO 98/55165) entitled "Cardiac Assist Device", a device comprising a cup and an internal diaphragm wherein at least a portion of the diaphragm is made from a biointegrating material is described. This device is designed to maximise affixation of the device to the heart by enabling vascularised tissue infiltration into the device. Preferably, the biointegrating material of the diaphragm integrates with the surface of the heart muscle to such an extent that a vacuum or other such means of securement is not required. It is believed that the use of a biointegrating material on the surface of the diaphragm minimises the risk of infection, and rejection of the device by the host's defence system. The device is reliant, however, on a bulky, cup-like structure and requires traditional surgical technique for placement. Such devices may also constrict the heart causing impairment of its filling and proper relaxation. This may also impede blood supply to the heart muscle via the coronary circulation.

DISCLOSURE OF THE INVENTION

According to one aspect of the present invention there is provided a heart actuator device for use in heart assist apparatus, the device including a paddle-like main body, the main body including a heart compressing wall, which in use is adapted to be affixed to at least a region of the heart, and a distal wall, which in use is arranged to be distal that region of the heart, and the heart compressing wall being movable in a direction relatively away from the distal wall, so as, in use to compress at least that region of the heart thereby assisting movement of the heart wall.

In one preferred form, the paddle like main body includes two major walls secured to or integral with each other at the peripheral portions thereof, one of the major walls defining the heart compressing wall and the other defining the distal wall. Preferably, the heart compressing wall includes a heart compressing surface which is generally curved inwardly towards a central region of the main body when in a normally relaxed condition. Preferably, the distal wall has a distal surface which is curved outwardly when in a normally relaxed condition.

The device may further include a chamber within the main body between the heart compressing wall and second distal wall and which is adapted for the ingress or egress of fluid which causes the movement of the heart compressing surface.

In a preferred form, the main body is configured such that both the heart compressing wall and the distal wall are adapted to move in a direction relatively away from one another.

Preferably, the heart compressing wall and the distal wall of the main body are of the same material with different degrees of stiffness. In one preferred form, the distal wall, the outer rim of the compressing wall and the portion joining the compression wall and distal wall edges include a reinforcing material therein to provide for a greater degree of stiffness and durability relative to the heart compressing wall. The strength of the distal wall, which does not have the added support that is provided to the compressing wall by the heart wall when the paddle is inflated, is thus also enhanced.

According to one preferred embodiment, at least a portion of the heart compressing wall includes a biointegratable material surface which facilitates the ingrowth of vascularised cellular tissue elements on the wall, the ingrowth of tissue into the heart compressing wall serving to affix the heart compressing wall of the main body to the heart. Desirably, the distal wall includes a biointegratable material that promotes vascularised cellular ingrowth into the distal wall which is thus adapted to integrate into surrounding tissue. The biointegratable material may for example be in the form of woven Tecoflex™ mesh. Seare Biomatrix™ or Gore-Tex DualMesh Biomaterial™.

In one preferred form, the paddle-like main body is deformable so as to be capable of undergoing a change from a first configuration to a second configuration. Preferably, the paddle-like main body includes a shape memory material which permits said deformation and subsequent return to its original shape.

Preferably, the main body includes a unitary structure formed of polyurethane, silicone or any other suitable material.

According to a preferred embodiment, the device may include means to monitor the cycle of a heart. The device may for example be adapted to be activated during systole or diastole of the heart. The monitoring means may include an electrocardiogram electrode operatively connected to at least a region of the surface of a heart and the electrical signals received from the electrodes transmitted to a cardiotachometer for the detection of heart rate, beat-to-beat interval or other native electrical activity of the ventricles.

The device according to a preferred embodiment may include one or more sensors adapted to measure the heart dimensions and excursion of the paddle walls during the cardiac cycle. Preferably, the or each sensor is a piezoelectric sensor. One example of a preferred form of sensor is a sonomicrometer. Preferably, there are a plurality of sensors operatively connected in selective positions to the heart compressing wall.

In a preferred form, the heart compressing wall is configured so that the heart compressing surface generally conforms to the shape of that region of the heart to which it is fixed.

The heart compressing wall may be adapted to be affixed to a region of either the left ventricle and/or the right ventricle of the heart.

According to another aspect of the present invention there is provided heart assist apparatus including one or more heart actuator devices as described above which are adapted to be secured to a region or selected regions of the heart, said apparatus further including driving means in fluid communication with the chamber. Preferably, there is provided a plurality of said heart actuator devices operatively connected to selected regions of the heart.

Preferably, the driving means is a hydraulic driving means. In another form it may be a pneumatic driving means.

In a preferred embodiment, the heart compressing wall is adapted to remain affixed with at least the aforementioned region of the heart regardless of any variation in the heart's condition. As described, previously known devices for assisting a failing heart have relied upon the principle of partially encasing at least the lower regions of a heart in a cup or other similarly rigid device. Internal the cup, such devices have a membrane or diaphragm which may be activated to compress the heart. One problem associated with such devices is related to obtaining the best fit of the device to a heart that is already enlarged and flaccid. When the heart is so enlarged, the device in being placed around the heart can create a situation similar to constrictive pericarditis or cardiac tamponade, conditions which can cause severe impairment of the heart's pumping action due to external restriction that compromises filling of the blood chambers. This condition is likely to worsen when a layer of fibrous tissue is caused to grow around the heart because of a tissue reaction in response to the surrounding foreign material. When the device is of such a size that the heart is fitted too loosely in the cup, the pumping action of the diaphragm acts to thump the surface of the heart during systolic assist. This poses a threat of bruising the heart and is also energetically highly inefficient According to available evidence from clinical and experimental use of mechanical cardiac assist devices, it is likely that the heart will become smaller (a process termed reverse remodelling of the heart) as a result of their use. This process involves some recovery of the muscle cells of the heart allowing the heart chambers to revert towards a more favourable pumping geometry. With use of a rigid cup employing a one piece diaphragm or several linked chambers to secure compression of the heart, reverse remodelling is unlikely to be facilitated even if the diaphragm is affixed to the heart. Further, if the diaphragm is affixed to the heart with this implementation, it is likely to hinder any residual contraction of the native heart.

On the other hand, using one or more devices according to the invention and affixing the heart compressing wall thereof to the heart surface in a manner that does not hinder the normal contractile geometry of the ventricles, accommodates the improvement in heart condition that occurs with reverse remodelling. Means of affixing the heart compressing surface to the heart surface are discussed in more detail below.

In one embodiment, a majority and in some cases the entire heart compressing wall may be affixed to the aforementioned region of the heart.

As mentioned, the shape of the devices can be configured to suit the region of the heart to which the device is to be affixed.

As discussed earlier the heart compressing wall and/or the distal wall can be curved relative to a notional lateral and/or longitudinal plane. The curvature is preferably selected to suit the curvature of the region of the heart to which it is to be affixed. According to yet another aspect of the present invention there is provided a method of assisting a failing heart using a heart actuator device as described above, the method including the steps of:

(a) positioning the heart compressing wall of the device at least adjacent a region of the heart;

(b) affixing the heart compressing wall to the region of the heart: and (c) applying fluid pressure to the chamber of the device such that the heart compressing wall compresses the heart wall in the region of the heart to which the device affixed.

According to yet another aspect of the present invention there is provided a method of introducing a device as described above to the heart of a patient, the method including the steps of:

(a) making an incision or puncture in the chest of a patient to allow access to the heart:

(b) inserting the device through the incision or puncture;

(c) affixing the heart compressing wall of the device to a region of the heart; and (d) applying fluid pressure to the chamber of the device such that the heart compressing wall compresses the heart wall in the region of the heart to which the device is affixed.

In one embodiment of this aspect of the invention, the device is inserted by firstly inserting a cannula through a port in the body and then passing the device through the cannula. In this embodiment, the device is preferably in a first closed configuration at least while it is internal the cannula. When positioned adjacent the region of the heart with which the paddle is to be affixed, the paddle is ejected from the cannula by a push rod or other like device whereupon it can take on a second expanded configuration. The cannula can then be withdrawn through the port before it is in turn removed.

In another embodiment of this aspect of the invention, the device may initially be held in place by a covering means such as a mesh that will wrap around the paddle and the heart. If desired, a suitable tissue glue can also be used to either affix the heart compressing surface to the heart or to enhance affixation provided by the covering means. Once sufficient cellular ingrowth has occurred, the covering means may be removed from around the heart. Alternatively, the covering means may be made from a biocompatible resiliently flexible material which may remain in place around the heart and the paddle. It is important that the covering means is made from a suitable flexible material, however, to allow for any change in the heart's condition, including variation in its size, shape or configuration. In a still further embodiment, the covering means may be made from a biodegradable material that is progressively resorbed by the body over a period of time.

The device in all aspects of the invention is preferably adapted such that it may be introduced into the patient and proximate the heart using minimally invasive or endoscopic surgery. It will, however, be appreciated that the device may be introduced through a thoracotomy.

BRIEF DESCRIPTION OF THE DRAWINGS

Preferred embodiments of the invention will hereinafter be described with reference to the following drawings.

BEST MODE OF CARRYING OUT THE INVENTION

Figure 1:
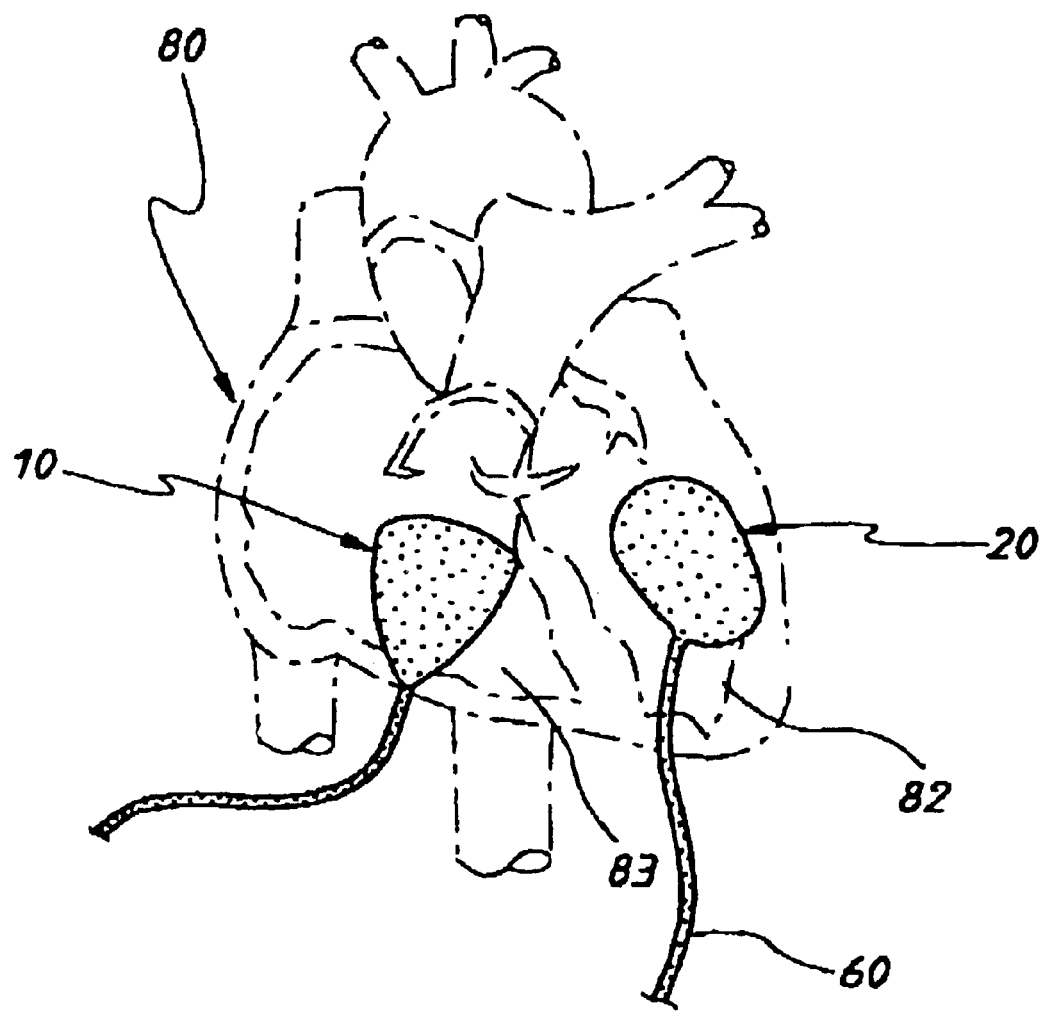
FIG. 1 is a schematic representation of a heart with two devices according to the present invention in position against the surface of the heart.
Figure 4:
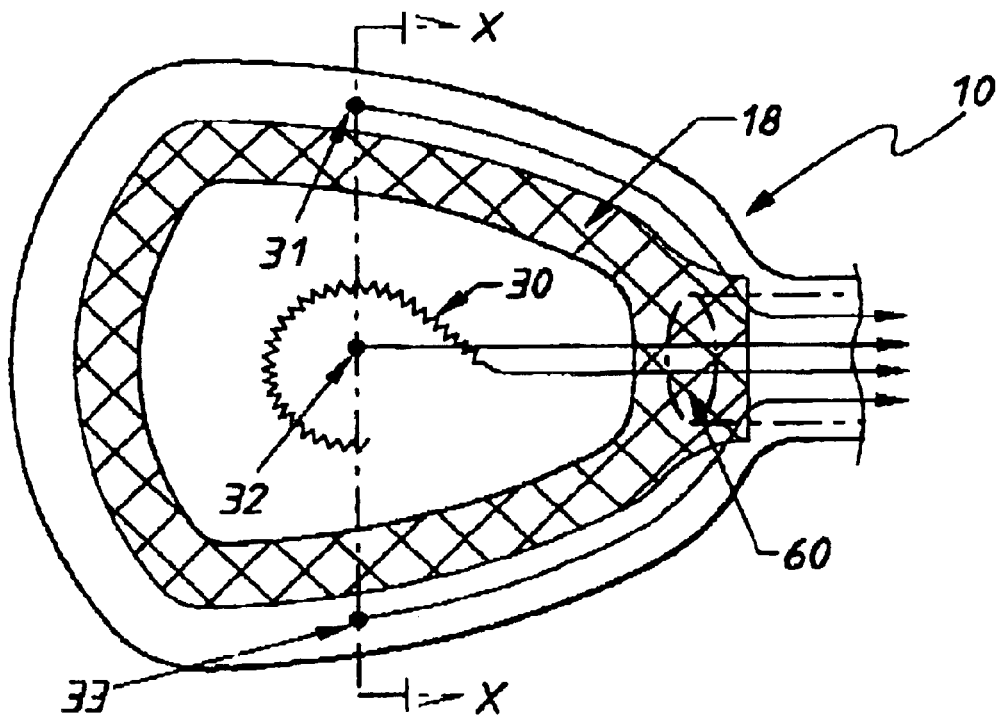
FIG. 4 is a schematic front elevational view of the device of the invention.
Figure 5:
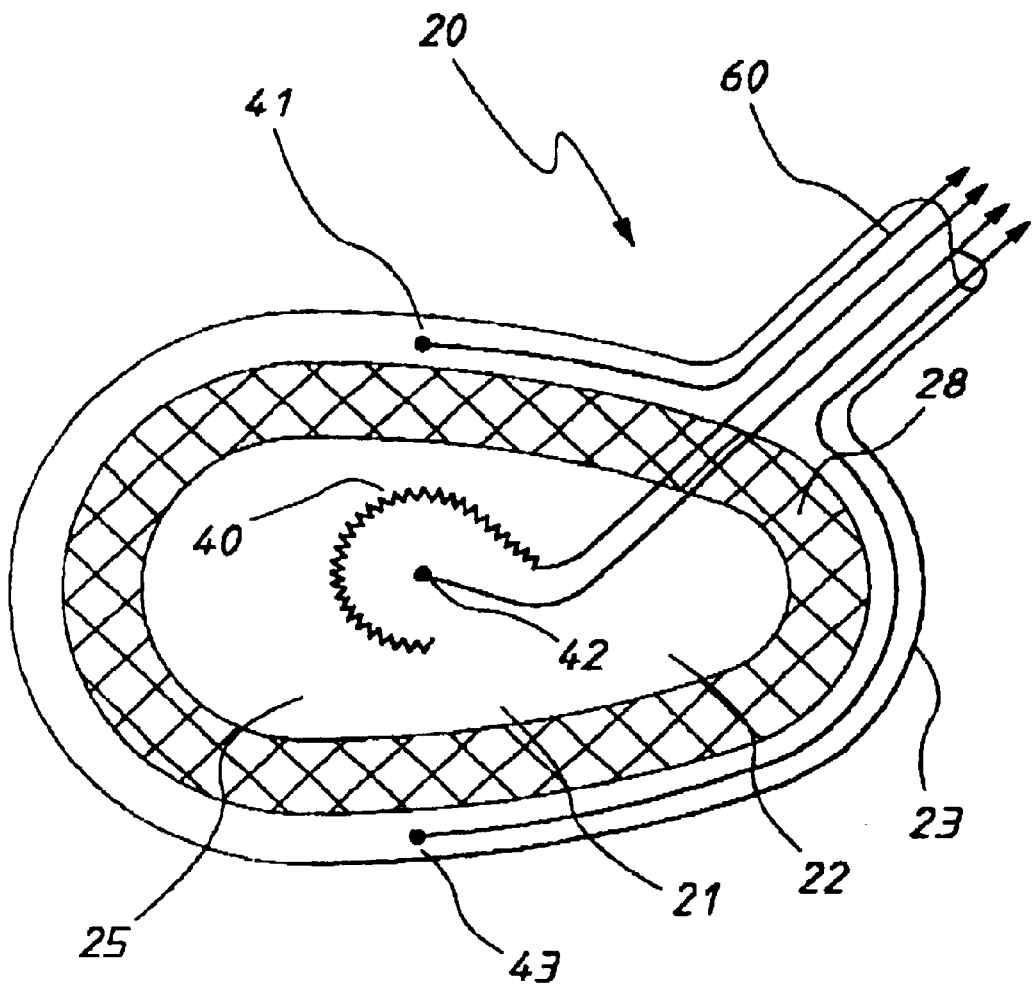
FIG. 5 is a schematic front elevational view of another embodiment of the invention.

Referring to FIG. 1 of the drawings there is shown a part of a heart assist apparatus applied to a heart 80 having a left ventricle 82 and a right ventricle 83. The apparatus shown includes two heart actuator devices 10 and 20, one of which is affixed to the right ventricle 83 and the other is affixed to the left ventricle 82 of the heart 80. As best seen in FIGS. 4 and 5 the devices 10 and 20 for affixing to the right and left ventricles of the heart differ in configuration but are generally of the same structure.

Figure 2:
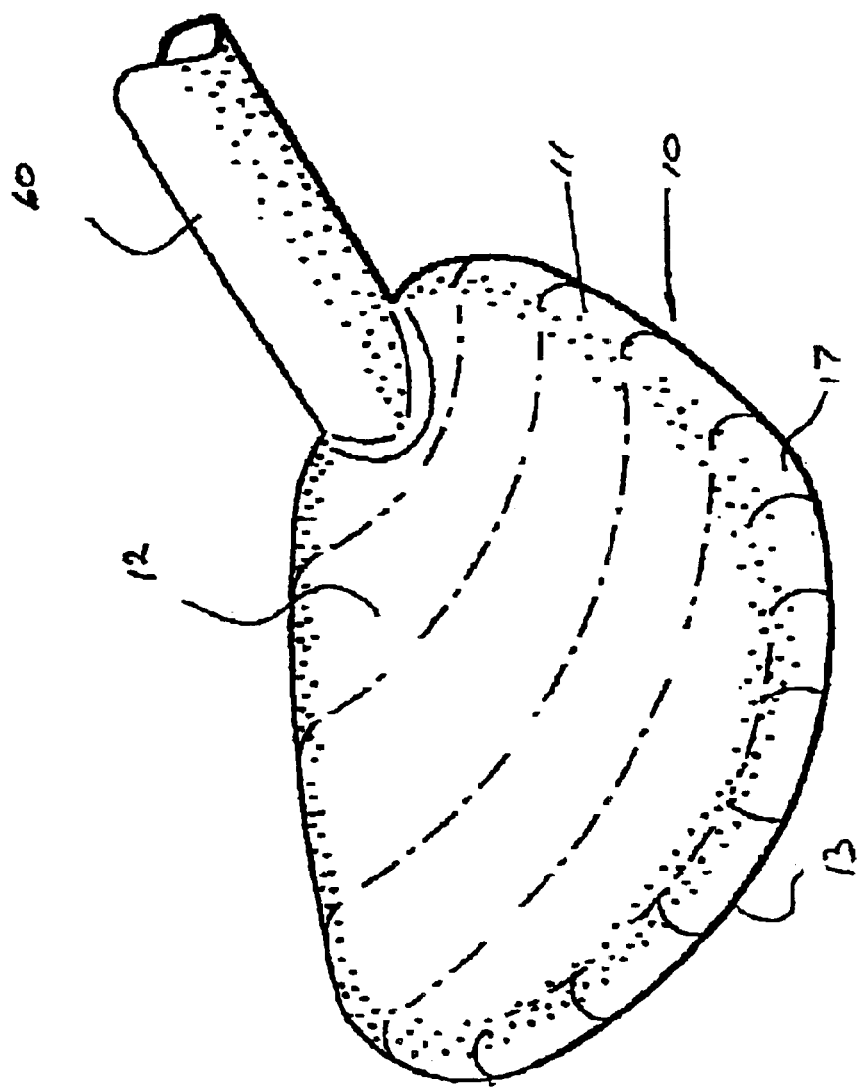
FIG. 2 is a perspective view of one form of the device according to the invention.
Figure 3:
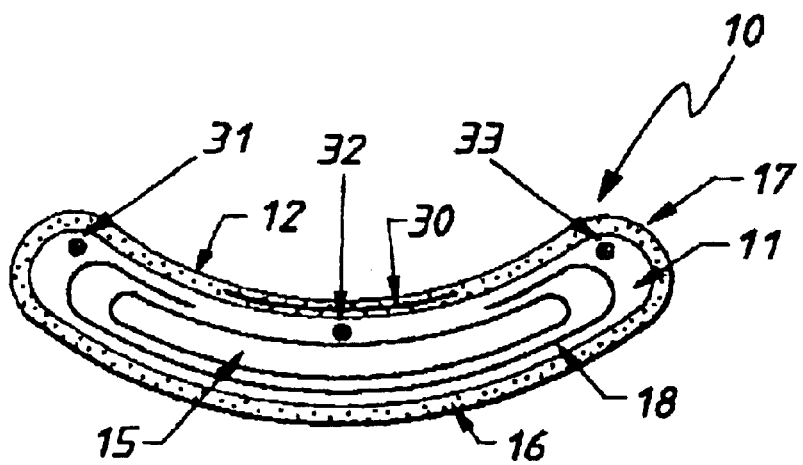
FIG. 3 is a cross-sectional view through X—X of FIG. 4 depicting the device of the invention in a collapsed state.

Referring to FIGS. 2 to 4 of the drawings, there is shown one embodiment of the heart actuator device which is particularly suited for attachment to the right ventricle. The heart actuator device 10 which comprises a paddle-like body 11 having a heart compressing wall 12 which is adapted to be affixed to a region of the surface of the right ventricle of the heart and a distal wall 13 which is positioned distal the surface of the heart. As shown in FIGS. 2&3 the device 10 is generally triangular in shape with walls 12 and 13 being in the form of major walls joined by a peripheral edge portion 17. As best seen in FIG. 3 both of the walls 12 and 13 are curved. This is particularly advantageous insofar as the heart compressing wall 12 is concerned because the curved nature of the wall inhibits stretching of the wall during movement thereof as described below.

The walls 12 and 13 have a chamber 15 therebetween, the chamber 15 being in fluid communication with a driver (not shown) which generates either hydraulic or pneumatic pressure. When the driver is activated pressure builds up in the chamber 15 causing both walls 12 and 13 to be moved relatively away from one another. The driver, controller or powersource can be positioned either internal or external the body of a patient receiving the device 10.

Chamber 15 is in fluid communication with the driver by way of tube 60 which is made from a suitably resiliently flexible material to facilitate insertion of the device 10 into the chest cavity of a patient whist still maintaining its tubular shape. This is a most desirable feature as any kinking of the tube would block the communication between chamber 15 and the driver thereby preventing the application of pressure to the walls of the device.

The body 11 of the device has a reinforcing mesh 18 incorporated primarily into the distal wall 13. As best seen in FIG. 3 the mesh 18 extends around the region of the peripheral portion 17 into the heart compressing wall 12.

The walls 12 and 13 have thereon a layer of biointegrating material 16 which facilitates the ingrowth of vascularised cellular tissue elements into the device. The cellular ingrowth of tissue secures the device to the surface of the heart avoiding the need to use suturing or various adhesives. In addition to securing the device to the surface of the heart, the likelihood of rejection of device by the heart and surrounding tissue is also reduced. The biointegration of the heart tissue with the device is also an advantageous feature for transmission of biopotential information such as the heart's electrical activity to the electrode 30 located in the wall 12 of the device, and for transmission of the ultrasound signals gathered from the piezoelectric sensors or sonomicrometers 31, 32, 33. Furthermore, because the heart tissue biointegrates with the device there is a markedly lessened chance of 'fibrous capsule' formation and the incidence of infection is greatly reduced. This is particular desirable feature as 30% of failures of mechanical assist devices result from infection.

The ability to place an individual device adjacent a specific portion of a heart is of great significance especially when it is understood that the chambers of the heart differ considerably in both function and anatomy.

The left ventricle is the chamber of the heart which receives oxygenated blood from the lungs. The function of the left ventricle is to pump this oxygenated blood to the entire body which requires a greater force of ejection. The blood inside the left ventricle is therefore under a greater pressure than in the right ventricle (about six times higher), the right ventricle simply having to pump de-oxygenated blood as far as the lungs. To obtain a sufficient ejection of blood, the muscular wall of the left ventricle must vigorously contract against the blood filled chamber. Accordingly, the walls of the left ventricle are much thicker and in fact, about three times thicker than the walls of the right ventricle.

If a device is to provide adequate assistance to a failing left ventricle it must apply a sufficient force upon the ventricle to eject a volume of blood at a sufficient pressure to reach the entire body. On the other hand, a failing right ventricle requires much less device force to eject the blood within the chamber to the lungs.

The present invention enables separate and individually controlled devices 10 and 20 to be positioned against the right and the left ventricles. Accordingly, less pressure may be applied to device 10 positioned on the right ventricle 83 than to device 20 positioned on the left ventricle 82.

The anatomy of the left and right ventricular chambers also differs substantially. In cross-section, the left ventricle is circular whereas the right ventricle is crescentic due to the bulging of the interventricular septum (the wall which divides the left and the right ventricles) into the cavity of the right ventricle. The difference in anatomy of the two ventricles calls for a particular structure of device to ensure optimal fit and performance.

FIG. 5 shows a device 20 particularly suitable for use in respect of the left ventricle. The device 20 is of the same general structure as device 10 although it is different in shape. Device 20 includes a paddle-like body 21 having a heart compressing wall 22 and a distal wall 23. The walls are curved in a similar fashion to those of device 10. A chamber 25 is disposed between the walls and functions in the same manner as described with reference to device 10.

In use the devices are small enough to be inserted by endoscopic or some other form of minimally invasive surgery. The devices may be made from a material that can adopt several different configurations and in preferred embodiments, the devices may be constructed of a 'shape memory' flexible material such as polyurethane or it may include within its structure a memory shape material, such as a Nitinol™ wire, threaded around its periphery. The device may be inserted into a cannula or some other delivery device in a closed configuration. The cannula is then introduced into the chest cavity through a puncture or incision and when in position adjacent the portion of heart to be assisted, the paddle is disposed from the end of the cannula. Once free of the cannula, the device takes on an expanded configuration such that the wall is caused to engage with the adjacent portion of heart.

When the device is in place proximate the heart, an elastic mesh (not shown) or other like flexible material may be placed around the heart thereby initially securing the device to the heart surface. The elastic mesh may be removed upon integration of the heart tissue with the device. Alternatively, the mesh may be made from a biodegradable material which over time will be broken down and resorbed by the body.

The heart actuator device as depicted herein may be activated during systole or diastole of the heart or at any other predetermined interval where the heart rhythm is chaotic or absent. The actuator device can be activated in early systole, in mid systole, in late systole, or throughout systole.

The devices 10 and 20 can include a monitoring means that monitors the native electrical activity of the heart of the patient. Such a monitoring means can be an electrocardiogram (ECG). In this case, an ECG electrode 30 or 40 is connected to at least a region of the surface of a heart and the electrical signals received from the ECG electrode transmitted to a cardiotachometer for the detection of heart rate or beat-to-beat interval (in milliseconds) or other electrical activity emanating from the heart. Exponential and derivative enhancement techniques are used to assure discrimination of the ECG's R-wave. Wide dynamic gain range and adjustable latency time prevent false triggering. The natural heart rate is used in a feedback loop to control intensity of heart assist. If predetermined heart rate limits are exceeded the control system automatically switches to fixed rate or variable ratio assist. Specifications of this part of the control system include the following: (1) usable rate range 10 to 500 beats per minute (bpm) (2) usable interval range 1 ms to 10s (3) measurement resolution 1 ms (interval), 0.1 bpm (rate) (4) latency time adjustment range from 50 ms to 1 s or more. The monitoring of the heart in this way enables the heart assist device to be activated or deactivated at a particular desired time in the natural cycle of a heart or at a fixed interval in case of a chaotic heart rhythm such as ventricular fibrillation or where there is lack of any intrinsic ventricular rhythm as in asystole.

As shown, each of the devices 10 and 20 may have a plurality of piezoelectric sensors in the form of sonomicrometers 31, 32, 33, 41, 42, 43 which are adapted to measure the heart dimensions and the movement of the device walls during the cardiac cycle. The piezoelectric sensors can be formed from a piezoelectric crystal or piezoelectric plastics material (e.g. polyvinylidene fluoride). In the case of a crystal, the surface area of each sensor is preferably about 1 mm$^2$. The sensors provide a signal output to a signal receiving means, that like the driver can be located internal or external the body. If required, a power source for the sensors can also be provided internal or external the body. The signals of the sensors can be detected by the signal receiving means using a signal communication system. The communication system could also be used to activate the sensors such that they only provide signal outputs on demand.

If required, the signals once received by the signal receiving means can be transmitted through a data transmission network for analysis at a distal location. For example, a physician could arrange for the download of signals of the sensors of the device of a patient over the data transmission network and provide an analysis of these signals without any requirement for the patient to visit the physician.

The dimensions measured by the sensors might include ventricular dimensions, including end-systolic and end-diastolic dimensions, segmental dimensions and cross-sectional dimensions and movement or displacement characteristics of the devices. By the measurement of such dimensions, the signal receiving means or another device using signals output by the signal receiving means can be used to determine heart performance characteristics, including the ventricular volume, stroke volume, ejection fraction percentage and cardiac output of the heart The sensors can be used to monitor variation in heart performance in response to different sequences of deflection of the walls of the devices. This can be used to allow determination of the optimal sequence of deflection of the devices and also allow the device to vary the sequence in response to changes in the heart cycle. The sequence of deflection of the devices can be adjusted in a number of ways, including:

the ratio of assisted to non-assisted beats; and the electromechanical delay between native atrial (electrical) heart activation and deflection of the paddles.

In the case of a chaotic native heart rhythm the actuation can be a fixed pattern or 10 one based on specific predetermined algorithms.

The sensors can be particularly useful in detecting the onset of ventricular fibrillation which can at times be hard to detect with routine ECG signal monitoring.

The signals output by the sensors may also be used to set and adjust the degree of pressurisation of the devices and the rate of rise and decay of pressure in the devices.

Optimisation of the settings of the device pressurisation, preferably in the presence of a physician, can be done in response to (a) exercise performed by the patient, or (b) by pacing the heart using an ECO electrode attached to the heart. The ECG electrode may be typically implanted at the time of device implantation or may be already in place. A pacemaker that is inserted under the skin of the patient can be used to provide the necessary stimulation to the ECG electrode to pace the heart. The electrical stimulation provided by the pacemaker when it is implanted, can also be used as the trigger for the pressurisation sequence of the devices.

Figure 6:
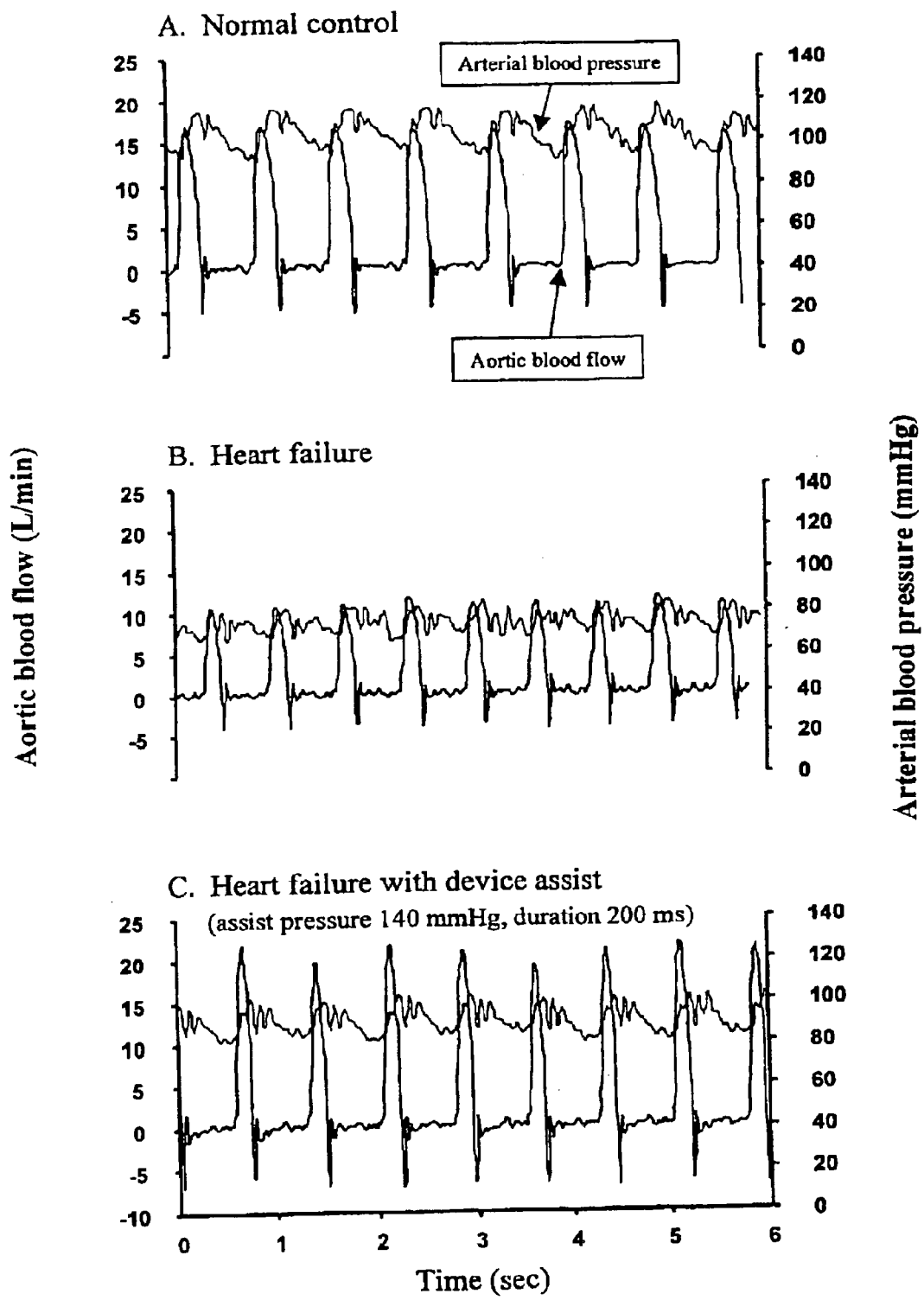
FIG. 6 are tracings of physiological parameters showing the effect of the device of the present invention on both a normal and a failing heart.

Referring to FIG. 6, the top panel A, arterial blood pressure (mean 104 mmHg) and aortic blood flow (BF, 4.02 L/min) were recorded under normal physiological conditions in a sheep with a device implanted. Referring now to panel B, there is shown the situation after stable heart failure has been induced by intravenous infusion of the beta adrenergic receptor antagonist Esmolol™. Arterial pressure decreased by 36% to 67 mmHg and BF decreased 40% to 2.42 L/min. Finally, panel C illustrates a situation when the failing heart was assisted by the device pressurised to 140 mmHg for 200 ms, the arterial pressure and BF rose to 90 mmHg and 3.54 L/min respectively.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The reference to any prior art in this specification is not, and should not be taken as, an acknowledgement or any form of suggestion that that prior art forms part of the common general knowledge in Australia.

What is claimed is:

1. A heart actuator device for use in heart assist apparatus, the device including a paddle-like main body, the main body including a proximal wall adapted to be affixed to at least a region of the heart, and a distal wall adapted to be distal that region of the heart, and the proximal wall being movable in a direction relatively away from the distal wall, so as, in use to compress at least that region of the heart and being movable in a direction relatively toward the distal wall, so as, in use to pull at least that region of the heart in a direction relatively toward the distal wall and thereby decompress at least that region of the heart thereby assisting movement of the heart wall.

2. A device according to claim 1 wherein said paddle-like main body includes two major walls secured to or integral with each other at the peripheral portions thereof, one of said major walls defining said proximal wall and the other defining said distal wall.

3. A device according to claim 1 wherein said proximal wall is generally curved inwardly towards the distal wall when in a normally relaxed condition.

4. A device according to claim 3 wherein the said distal wall is curved outwardly when in a normally relaxed condition.

5. A device according to claim 1 including a chamber within the main body between the proximal wall and said distal wall and being adapted for the ingress or egress of fluid which causes the movement of the proximal wall.

6. A device according to claim 1 wherein said main body is configured such that both the proximal wall and the distal wall are adapted to move in a direction relatively away from one another during compression of the heart.

7. A device according to claim 6 wherein the proximal wall and the distal wall of the main body are of materials with different degrees of stiffness.

8. A device according to claim 1 wherein the paddle-like main body is deformable so as to be capable of undergoing a change from a first configuration to a second configuration, said paddle-like main body including a shape memory material.

9. A device according to claim 1 wherein the main body includes a unitary structure formed of polyurethane or silicone, including reinforcement mesh or hardened material.

10. A device according to claim 1 including means to monitor the electrical and mechanical activity of the heart.

11. A device according to claim 10 wherein the device is activated so as to boost the pump output of the heart.

12. A device according to claim 11 wherein said monitoring means includes an electrocardiogram electrode operatively connected to at least a region of the surface of the heart and the electrical signals received from the electrodes are used to monitor the intrinsic electrical activity of the heart, these signals being also transmitted to a cardiotachometer for the detection of heart rate or beat-to-beat interval.

13. A device according to claim 12 wherein said ECG electrode is integrated into said proximal wall.

14. A device according to claim 1 including a plurality of sensors adapted to measure the heart dimensions and movement or displacement of the chamber walls during excursion of the devices.

15. A device according to claim 14 wherein each sensor is a piezoelectric sensor.

16. A device according to claim 15 wherein each sensor is a sonomicrometer.

17. A device according to claim 14 wherein there are a plurality of said sensors operatively connected in selective positions to said proximal wall.

18. A device according to claim 1 wherein said proximal wall is configured so that the proximal surface generally conforms to the shape of that region of the heart to which it is fixed.

19. A device according to claim 1 wherein said proximal wall is adapted to be affixed to a region of the left ventricle of the heart.

20. A device according to claim 1 wherein said proximal wall is adapted to be fixed to a region of the right ventricle of the heart.

21. A device according to claim 1 wherein the main body is at least initially affixed to the heart by straps.

22. Heart assist apparatus including one or more heart actuator devices according to claim 1 which are adapted to be secured to a region or selected regions of the heart, said apparatus further including driving means in fluid communication with the chamber, said driving means including a controller and a power source.

23. Apparatus according to claim 22 wherein said driving means is a hydraulic driving apparatus.

24. Apparatus according to claim 22 wherein said driving means is a pneumatic driving means.

25. Apparatus according to claim 22 wherein there is provided a plurality of said heart actuator devices operatively connected to selected regions of the heart.

26. A method of assisting a failing heart using a heart actuator device according to claim 1, the method including the steps of:
 (a) positioning the proximal wall of the device at least adjacent a region of the heart;
 (b) affixing the proximal wall with the region of the heart; and
 (c) applying fluid pressure to the chamber of the device such that the proximal wall compresses the heart wall in the region of the heart to which the device is affixed.

27. A method of introducing a device according to claim 1 to the heart of a patient, the method including the steps of:
 (a) making an incision or puncture in the chest of a patient to allow access to the heart;
 (b) inserting the device through the incision or puncture;
 (c) affixing the proximal wall to a region of the heart; and
 (d) applying fluid pressure to the chamber of the device such that the proximal wall compresses the heart wall in the region of the heart to which the device is affixed.

28. A heart actuator device for use in heart assist apparatus, the device including a paddle-like main body, the main body including a heart compressing wall, which in use is adapted to be affixed to at least a region of the heart, and a distal wall, which in use is adapted to be distal that region of the heart, and both the heart compressing wall and the distal wall being movable in a direction relatively away from one another during compression of the heart, so as, in use to compress at least that region of the heart thereby assisting movement of the heart wall, the heart compressing wall and the distal wall of the main body being of materials with different degrees of stiffness, the distal wall including a reinforcing material therein to provide for a greater degree of stiffness relative to the heart compressing wall.

29. A device according to claim 28 wherein said reinforcing material extends through the peripheral portions of the device into the heart compressing wall.

30. A heart actuator device for use in heart assist apparatus, the device including a paddle-like main body, the main body including a heart compressing wall, which in use is adapted to be affixed to at least a region of the heart, and a distal wall, which in use is adapted to be distal that region o the heart, and the heart compressing wall being movable in a direction relatively away from the distal wall, so as, in use to compress at least that region of the heart thereby assisting movement of the heart wall, at least a portion of the heart compressing wall including a biointegratable material surface which facilitates the ingrowth of vascularised cellular tissue elements into the wall, the ingrowth of tissue into the heart compressing surface serving to affix the heart compressing wall of the main body to the heart.

31. A device according to claim 30 wherein the distal wall includes a biointegratable material that promotes vascularised cellular growth into said distal wall so that it integrates into surrounding tissue.

* * * * *